United States Patent
Woo et al.

(10) Patent No.: US 9,534,069 B2
(45) Date of Patent: Jan. 3, 2017

(54) PHOTOCURABLE COMPOSITION, BARRIER LAYER COMPRISING SAME, AND ENCAPSULATED DEVICE COMPRISING SAME

(71) Applicant: CHEIL INDUSTRIES, INC., Gumi-si, Gyeongsangbuk-do (KR)

(72) Inventors: Chang Soo Woo, Uiwang-si (KR); Seung Woo Chang, Uiwang-si (KR); Hwan Sung Chun, Uiwang-si (KR); Seung Jib Choi, Uiwang-si (KR)

(73) Assignee: Cheil Industries, Inc., Gumi-Si, Gyeongsangbuk-do (KR)

( * ) Notice: Subject to any disclaimer, the term of this patent is extended or adjusted under 35 U.S.C. 154(b) by 0 days.

(21) Appl. No.: 14/759,066

(22) PCT Filed: Sep. 30, 2013

(86) PCT No.: PCT/KR2013/008755
§ 371 (c)(1),
(2) Date: Jul. 2, 2015

(87) PCT Pub. No.: WO2014/109455
PCT Pub. Date: Jul. 17, 2014

(65) Prior Publication Data
US 2015/0353668 A1    Dec. 10, 2015

(30) Foreign Application Priority Data

Jan. 11, 2013  (KR) .................. 10-2013-0003677

(51) Int. Cl.
| | |
|---|---|
| *C08F 230/08* | (2006.01) |
| *C08L 71/02* | (2006.01) |
| *C07F 7/18* | (2006.01) |
| *C08F 130/08* | (2006.01) |
| *H01L 51/00* | (2006.01) |
| *C08G 77/20* | (2006.01) |
| *C08L 83/04* | (2006.01) |
| *G03F 7/027* | (2006.01) |
| *H01L 51/52* | (2006.01) |
| *C08G 65/336* | (2006.01) |

(52) U.S. Cl.
CPC .......... *C08F 230/08* (2013.01); *C07F 7/1844* (2013.01); *C08F 130/08* (2013.01); *C08G 77/20* (2013.01); *C08L 71/02* (2013.01); *C08L 83/04* (2013.01); *G03F 7/027* (2013.01); *H01L 51/0094* (2013.01); *H01L 51/5253* (2013.01); *C08G 65/336* (2013.01); *H01L 51/0034* (2013.01)

(58) Field of Classification Search
None
See application file for complete search history.

(56) References Cited

U.S. PATENT DOCUMENTS 5,596,038 A * 1/1997 Subramaniam ....... C08F 230/08
                                                           524/388
8,334,039 B2    12/2012 Aoki et al.

FOREIGN PATENT DOCUMENTS

| EP | 1202373 A2 | 5/2002 |
|---|---|---|
| JP | 9-77781 * | 3/1997 |
| JP | 2004-002733 A | 1/2004 |
| KR | 2005-0016585 A | 2/2005 |
| KR | 2010-0073033 A | 7/2010 |
| KR | 2011-0069094 A | 6/2011 |

OTHER PUBLICATIONS

Die shear strength test method from the Institute for Interconnecting and Packaging Electroniuc Circuits (no date).*
Epoxy Adhesive Application Guide from Epotek, section on evaluating die shear strength (no date).*

* cited by examiner

*Primary Examiner* — Marc Zimmer
(74) *Attorney, Agent, or Firm* — Lee & Morse, P.C.

(57) ABSTRACT

The present invention relates to: a photocurable composition comprising a silicone-based compound having a repeating unit represented by the chemical formula A (linear or branched alkylene oxide having a carbon number 1-15) and a photocurable functional group; a barrier layer comprising the same; and an encapsulated device comprising the barrier layer.

14 Claims, 1 Drawing Sheet

PHOTOCURABLE COMPOSITION, BARRIER LAYER COMPRISING SAME, AND ENCAPSULATED DEVICE COMPRISING SAME

CROSS REFERENCE TO RELATED APPLICATIONS

This is the U.S. national phase application based on PCT Application No. PCT/KR2013/008755, filed Sep. 30, 2013, which is based on Korean Patent Application No. 10-2013-0003677, filed Jan. 11, 2013, the entire contents of all of which are hereby incorporated by reference.

TECHNICAL FIELD

The present invention relates to a photocurable composition, a barrier layer including the same, and an encapsulated apparatus including the same.

BACKGROUND ART

Organic optoelectronic devices such as organic light emitting diodes, devices including photovoltaic cells, and displays such as organic thin film transistors must be encapsulated to protect sensitive components thereof from gases in air (mainly oxygen and/or water vapor). Improper protection can cause deterioration in quality of the devices. In addition, this can cause occurrence of non-radial dark spots, which also lead to degradation of the devices. In particular, in an organic light emitting diode, water vapor can cause degradation of the diode and deterioration in quality of an interface between an anode (or cathode) and an organic film.

DISCLOSURE

Technical Problem

It is an aspect of the present invention to provide a photocurable composition capable of forming a barrier layer encapsulating a member for an apparatus susceptible to environmental factors.

It is another aspect of the present invention to provide a photocurable composition which exhibits high photocuring rate and forms an encapsulating barrier layer having high adhesion to an inorganic barrier layer and high reliability.

It is a further aspect of the present invention to provide a barrier layer formed using the photocurable composition as set forth above and an encapsulated apparatus including the same.

Technical Solution

In accordance with one aspect of the present invention, a photocurable composition may include: (A) a silicon-based compound including a repeating unit represented by Formula A and a photocurable functional group:

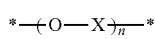
<Formula A>

(wherein Formula A, *, X, and n are the same as those described in the following detailed description of the invention).

The photocurable composition may have a die share strength of about 28 kgf/(mm)$^2$ to about 50 kgf/(mm)$^2$ with respect to an inorganic barrier layer after curing, and include the (A) silicon-based compound including the repeating unit represented by Formula A and the photocurable functional group.

In accordance with another aspect of the present invention, a barrier layer may have an a die share strength to an inorganic barrier layer of about 28 kgf/(mm)$^2$ to about 50 kgf/(mm)$^2$, and may include a cured product of the photocurable composition.

In accordance with a further aspect of the present invention, an encapsulated apparatus may include a substrate; a member for the apparatus formed on the substrate; and a barrier stack formed on member for the apparatus and including an inorganic barrier layer and an organic barrier layer, wherein the organic barrier layer may have a die share strength to the inorganic barrier layer of about 28 kgf/(mm)$^2$ to about 50 kgf/(mm)$^2$.

Advantageous Effects

The present invention provides a photocurable composition which exhibits high photocuring rate, is capable of forming a barrier layer exhibiting high adhesion to an inorganic barrier layer and having high reliability, and can be used for encapsulation.

BEST MODE

Figure 1:
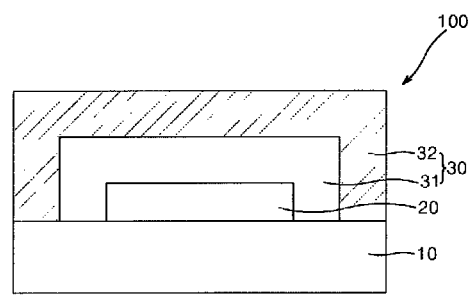
FIG. 1 is a cross-sectional view of an encapsulated apparatus according to one embodiment of the present invention.

As used herein, unless otherwise stated, the term 'substituted' in the phrase 'substituted or unsubstituted' means that at least one hydrogen atom among functional groups of the present invention is substituted with a halogen atom (F, Cl, Br or I), a hydroxyl group, a nitro group, a cyano group, an imino group (=NH, =NR (R: a $C_1$ to $C_{10}$ alkyl group)), an amino group (—$NH_2$, —NH(R'), —N(R")(R'''), where R', R" and R''' are each independently a $C_1$ to $C_{10}$ alkyl group), a $C_1$ to $C_{20}$ alkyl group, a $C_6$ to $C_{20}$ aryl group, a $C_3$ to $C_{10}$ cycloalkyl group, a $C_3$ to $C_{20}$ heteroaryl group, a $C_2$ to $C_{30}$ heterocycloalkyl group, or a $C_7$ to $C_{21}$ arylalkyl group; the term 'compound' means a monomer or an oligomer thereof; the term 'oligomer' means a polymer of corresponding monomers; the symbol '*' indicates a binding site between elements; and the term '(meth)acrylate' may refer to acrylate and/or methacrylate.

A photocurable composition according to one embodiment of the present invention may include (A) a silicon-based compound having a repeating unit represented by Formula A and one or more photocurable functional groups (for example: vinyl group or (meth)acrylate group):

<Formula A>

(wherein Formula A, * is a binding site to an element. X is a $C_1$ to $C_5$ linear or branched alkylene group, and n is an integer of 1 or more)

The silicon-based compound may be a monofunctional or polyfunctional compound, preferably a polyfunctional compound. Specifically, the silicon-based compound may be represented by Formula 1:

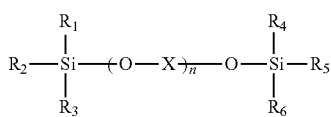
<Formula 1>

(wherein Formula 1, $R_1$, $R_2$, $R_3$, $R_4$, $R_5$, and $R_6$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ alkoxy group, or a substituted or unsubstituted $C_1$ to $C_{10}$ silyl group, or represented by Formula 2,

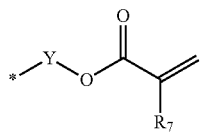
<Formula 2>

(wherein Formula 2, * is a binding site to an element, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group);

at least one of $R_1$, $R_2$, and $R_3$ is represented by Formula 2, at least one of $R_4$, $R_5$, and $R_6$ is represented by Formula 2, X is a $C_1$ to $C_5$ linear or branched alkylene group, and n is an integer of 1 or more).

Specifically, $R_1$, $R_2$, and $R_3$ may be each independently a $C_1$ to $C_{10}$ alkyl group or represented by Formula 2, $R_4$, $R_5$, and $R_6$ may be each independently a $C_1$ to $C_{10}$ alkyl group or represented by Formula 2, X may be a $C_1$ to $C_3$ linear or branched alkylene group, and n may be an integer of 1 to 10.

In one embodiment, the silicon-based compound of Formula 1 may include at least one of compounds represented by Formula 1-1 and Formula 1-2.

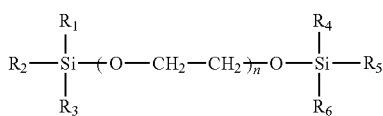
<Formula 1-1>

(wherein Formula 1-1, $R_1$, $R_2$, $R_3$, $R_4$, $R_5$, and $R_6$ are the same as defined in Formula 1, and n is an integer of 1 to 10)

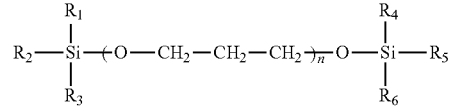
<Formula 1-2>

(wherein Formula 1-2, $R_1$, $R_2$, $R_3$, $R_4$, $R_5$, and $R_6$ are the same as defined in Formula 1, and n is an integer of 1 to 10).

The silicon-based compound may be prepared by a typical method in the art. For example, the silicon-based compound may be prepared by reacting a (meth)acrylate and a silicon-donor compound with a glycol-based compound.

In the photocurable composition, the silicon-based compound may be included, in terms of solid content, in an amount of about 1 wt % to about 99 wt %, preferably about 90 wt % to about 99 wt %, more preferably about 90 wt %, about 91 wt %, about 92 wt %, about 93 wt %, about 94 wt %, about 95 wt %, about 96 wt %, about 97 wt %, about 98 wt %, about 99 wt %, or about 10 wt % to about 80 wt %, or about 40 wt % to about 55 wt %, more preferably about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, or about 55 wt %. Within this range, the photocurable composition may have good photocuring rate and good adhesion while securing good reliability.

A photocurable composition according to another embodiment may include a silicon-based compound and an initiator. The photocurable composition according to this embodiment is substantially the same as the photocurable composition according to the above embodiment except for the initiator. Thus, the initiator will be described in more detail hereinafter.

As for the initiator, any typical photoinitiators capable of performing photocuring reaction in the art may be used without limitation. For example, the photo initiator may include triazine based initiators, acetophenone based initiators, benzophenone based initiators, thioxanthone based initiators, benzoin based initiators, phosphorus based initiators, oxime based initiators, and mixtures thereof. Preferably, the photo initiator may be a phosphorus based initiator. The phosphorus based initiator may include diphenyl(trimethylbenzoyl)phosphine oxide, or a mixture thereof, without being limited thereto.

In the photocurable composition, the initiator may be included, in terms of solid content, in an amount of about 1 wt % to about 99 wt %, preferably about 1 wt % to about 10 wt % or about 1 wt % to about 5 wt %, more preferably about 1 wt %, about 2 wt %, about 3 wt %, about 4 wt %, about 5 wt %, about 6 wt %, about 7 wt %, about 8 wt %, about 9 wt %, or about 10 wt %. Within this range, the initiator can secure sufficient photopolymerization upon exposure and prevent deterioration in transmittance due to the unreacted initiator after photopolymerization.

A photocurable composition according to a further embodiment may include a silicon-based compound, an initiator, and (C) a silicon-based compound not containing the repeating unit represented by Formula A. The photocurable composition according to this embodiment is substantially the same as the photocurable composition according to the above embodiment except for the (C) silicon-based compound not containing the repeating unit represented by Formula A. Thus, the (C) silicon-based compound not containing the repeating unit represented by Formula A will be mainly described hereinafter.

The (C) silicon-based compound can improve the photocuring rate, adhesion and reliability of the photocurable composition. Specifically, the (C) silicon-based compound may be a photocurable compound including a siloxane group and one or more photocurable functional groups (for example: vinyl group or (meth)acrylate group). Further, the (C) silicon-based compound may be a monofunctional or polyfunctional compound, preferably a polyfunctional compound. More specifically, the (C) silicon-based compound may be represented by Formula 3:

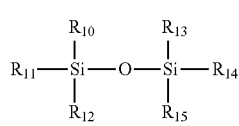
<Formula 3>

(wherein Formula 3, $R_{10}$, $R_{11}$, $R_{12}$, $R_{13}$, $R_{14}$, and $R_{15}$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ alkoxy group, or a substituted or unsubstituted $C_1$ to $C_{10}$ silyl group, or represented by Formula 2,

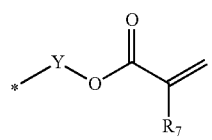
<Formula 2>

(wherein Formula 2, * is a binding site to an element, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group); at least one of $R_{10}$, $R_{11}$, and $R_{12}$ is represented by Formula 2; and at least one of $R_{13}$, $R_{14}$, and $R_{15}$ is represented by Formula 2).

Preferably, $R_{10}$, $R_{11}$, and $R_{12}$ may be each independently a $C_1$ to $C_{10}$ alkyl group or represented by Formula 2, and $R_{13}$, $R_{14}$, and $R_{15}$ may be each independently a $C_1$ to $C_5$ alkyl group or represented by Formula 2.

In one embodiment, the (C) silicon-based compound may be 1,3-bis((meth)acryloxyalkyl)tetraalkyldisiloxane or a mixture thereof. The (C) silicon-based compound may be prepared by synthesis or may be obtained from commercially available products.

In the photocurable composition, the (C) silicon-based compound may be included, in terms of solid content, in an amount of about 10 wt % to about 80 wt %, preferably about 40 wt % to about 55 wt %, more preferably about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, or about 55 wt %. Within this range, the photocurable composition can exhibit high photocuring rate and high adhesion while securing good reliability.

In one embodiment, the photocurable composition may include 100 wt % of (A) in term of solid content. In another embodiment, the photocurable composition may include about 1 wt % to about 99 wt % of (A) and about 1 wt % to about 99 wt % of (B), preferably about 90 wt % to about 99 wt % of (A) and about 1 wt % to about 10 wt % of (B), in term of solid content. In a further embodiment, the photocurable composition may include about 10 wt % to about 80 wt % of (A), about 1 wt % to about 10 wt % of (B), and about 10 wt % to about 80 wt % of (C), in term of solid content. Preferably, the photocurable composition may include about 40 wt % to about 55 wt % of (A), about 1 wt % to about 5 wt % of (B), and about 40 wt % to about 55 wt % of (C). Within this range, the photocurable composition can exhibit high photocuring rate and high adhesion while securing good reliability.

The photocurable composition may be prepared using the silicon-based compound or by mixing the silicon-based compound and the initiator. Preferably, the photocurable composition is formed as a solvent-free photocurable composition.

The photocurable composition may have a photocuring rate of about 90% or more. Within this range, the photocurable composition can form a layer which does not suffer from a shift by virtue of high shrinkage stress after curing and thus can be used for device encapsulation. Preferably, the photocurable composition may have a photocuring rate of about 93% to about 99%. The photocuring rate can be measured with reference to experimental examples described below.

The photocurable composition may have a die share strength to an inorganic barrier layer of about 28 kgf/(mm)$^2$ or more after curing. If the die share strength is less than 28 kgf/(mm)$^2$, external moisture or oxygen can easily permeate between the barrier layers, causing deterioration in reliability. The inorganic barrier layer may include an inorganic barrier layer (for example, SiO$_x$, SiN$_x$, and Al$_2$O$_3$) described below, without being limited thereto. Preferably, the photocurable composition has a die share strength to an inorganic barrier layer of about 28 kgf/(mm)$^2$ to about 50 kgf/(mm)$^2$ after curing.

In one embodiment, the photocurable composition may have a die share strength of about 32 kgf/(mm)$^2$ to about 50 kgf/(mm)$^2$ with respect to silicon oxide or aluminum oxide as the inorganic barrier layer. In another embodiment, the photocurable composition may have a die share strength of about 28 kgf/(mm)$^2$ to about 50 kgf/(mm)$^2$ with respect to silicon oxide as the inorganic barrier layer. The die share strength can be measured with reference to experimental examples described below.

The photocurable composition may have a light transmittance of about 95% or more after curing. Within this range, the photocurable composition can provide improved visibility when a display is encapsulated with the composition. Here, the transmittance is measured at a wavelength of 550 nm. Preferably, the photocurable composition has a light transmittance of about 95% to about 100%. The light transmittance can be measured with reference to experimental examples described below.

A member for an apparatus, particularly a member for displays, can suffer from degradation or deterioration in quality due to permeation of gas or liquid in a surrounding environment, for example, atmospheric oxygen, moisture and/or water vapor, and due to permeation of chemicals used in the preparation of electronic products. To prevent this problem, the member for an apparatus needs to be sealed or encapsulated. Examples of the member for an apparatus may include organic light emitting devices (OLEDs), illumination devices, flexible organic light emitting device displays, metal sensor pads, microdisc lasers, electrochromic devices, photochromic devices, microelectromechanical systems, solar cells, integrated circuits, charge coupled devices, light emitting polymers, and light emitting diodes, without being limited thereto.

The photocurable composition according to the present invention may form an organic barrier layer used for sealing or encapsulation of the apparatus, particularly, a flexible display.

An organic barrier layer according to the present invention may be formed of the photocurable composition. Specifically, the organic barrier layer may be formed by photocuring the photocurable composition. Although not limited to the following method, the organic barrier layer may be formed by coating the photocurable composition to a thickness of about 0.1 μm to about 20 μm, followed by irradiation at about 10 J/cm$^2$ to about 500 J/cm$^2$ for about 1 to 50 seconds.

The organic barrier layer has the aforementioned post-curing properties of the photocurable composition, and may form a barrier stack together with an inorganic barrier layer for encapsulation of an apparatus, as described below.

The barrier stack according to the present invention may include the organic barrier layer and the inorganic barrier layer.

The inorganic barrier layer includes different components from those of the organic barrier layer, thereby supplementing the effects of the organic barrier layer.

The inorganic barrier layer may be any inorganic barrier layer so long as the inorganic barrier layer can exhibit excellent light transmittance and excellent moisture and/or oxygen barrier properties. For example, the inorganic barrier layer may be formed of metals, nonmetals, compounds of metals or nonmetals, alloys of metals or nonmetals, oxides of metals, nonmetals or compounds thereof, fluorides of metals, nonmetals or compounds thereof, nitrides of metals, nonmetals or compounds thereof, carbides of metals, nonmetals or compounds thereof, oxynitrides of metals, nonmetals or compounds thereof, borides of metals, nonmetals or compounds thereof, oxyborides of metals, nonmetals or compounds thereof, silicides of metals, nonmetals or compounds thereof, or mixtures thereof. The metals or the nonmetals may include silicon (Si), aluminum (Al), selenium (Se), zinc (Zn), antimony (Sb), indium (In), germanium (Ge), tin (Sn), bismuth (Bi), transition metals, and lanthanide metals, without being limited thereto. Specifically, the inorganic barrier layer may be formed of $SiO_x$, $SiO_xN_y$, ZnSe, ZnO, $Sb_2O_3$, $Al_2O_3$, $In_2O_3$, $SnO_2$ (where x ranges from 1 to 5, y ranges from 1 to 5, and z ranges from 1 to 5), and the like.

The inorganic barrier layer and the organic barrier layer may be formed by a vacuum process, for example, sputtering, chemical vapor deposition, metal organic chemical vapor deposition, plasma chemical vapor deposition, evaporation, sublimation, electron cyclotron resonance-plasma enhanced chemical vapor deposition, or combinations thereof.

The organic barrier layer can secure the aforementioned properties. As a result, when the organic barrier layer and the inorganic barrier layer are alternately stacked one above another, the organic barrier layer can secure smoothness of the inorganic barrier layer. In addition, the organic barrier layer can prevent defects of one inorganic barrier layer from spreading to other inorganic barrier layers.

The barrier stack may include any number of organic and inorganic barrier layers. Combination of the organic and inorganic barrier layers may vary with a level of permeation resistance to oxygen, moisture, water vapor and/or chemicals.

In the barrier stack, the organic and inorganic barrier layers may be alternately deposited. This is because the organic barrier layer affects the inorganic barrier layer due to the properties of the photocurable composition. Accordingly, the organic barrier layer and the inorganic barrier can supplement or reinforce encapsulation of the display.

Preferably, each of the inorganic and organic barrier layers may be alternately deposited to be composed of two or more layers, wherein the number of times of deposition may be about 10 or less (for example, about 2 to 10 times), preferably about 7 or less (for example, about 2 to 7 times), more preferably to a 7-layer structure of an inorganic barrier layer-organic barrier layer-inorganic barrier layer-organic barrier layer-inorganic barrier layer-organic barrier layer-inorganic barrier layer.

In the barrier stack, each organic barrier layer may have a thickness of about 0.1 μm to about 20 μm, preferably about 1 μm to about 10 μm, and each inorganic barrier layer may have a thickness of about 5 nm to about 500 nm, preferably about 5 nm to about 200 nm.

The barrier stack is a thin encapsulating film and may have a thickness of about 5 μm or less, preferably about 1.5 μm to about 5 μm.

In accordance with a further aspect of the present invention, an encapsulated apparatus may include a member for the apparatus and a barrier stack formed on the member for the apparatus and including the barrier layer or barrier stack.

FIG. 1 is a cross-sectional view of an encapsulated apparatus according to one embodiment of the present invention.

Referring to FIG. 1, an encapsulated apparatus 100 according to one embodiment of the invention may include a substrate 10; a member for the apparatus (for example, an organic light emitting diode) 20 formed on the substrate 10; and a barrier stack 30 including an inorganic barrier layer 31 and an organic barrier layer 32 and formed on the member for the apparatus 20.

Figure 2:
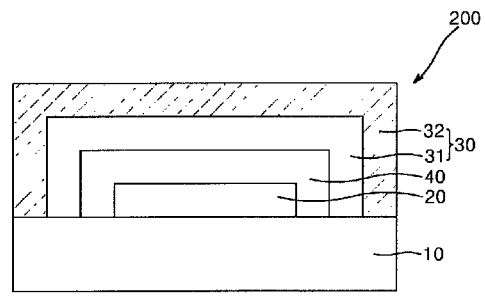
FIG. 2 is a cross-sectional view of an encapsulated apparatus according to another embodiment of the present invention.

FIG. 2 is a cross-sectional view of an encapsulated apparatus according to another embodiment of the present invention.

Referring to FIG. 2, an encapsulated apparatus 200 according to another embodiment of the invention may include a substrate 10; a member for the apparatus (for example, an organic light emitting diode) 20 formed on the substrate 10; and a barrier stack 30 including an inorganic barrier layer 31 and an organic barrier layer 32 and formed on the member for the apparatus 20.

FIG. 1 shows an embodiment in which the member for the apparatus 20 and the inorganic barrier layer 31 adjoin each other, and FIG. 2 shows an embodiment in which an empty space 40 is formed between the member for the apparatus 20 and the inorganic barrier layer 31.

Details of the member for the apparatus, the organic barrier layer, the inorganic barrier layer, and the barrier stack are the same as described above.

The substrate is not particularly limited so long as the member for the apparatus can be stacked on the substrate. For example, the substrate may be formed of a material, such as transparent glass, a plastic sheet, silicon, or a metal substrate.

The encapsulated apparatus may be formed by any typical method. The member for the apparatus is formed on a substrate, followed by forming an inorganic barrier layer on the member for the apparatus. The photocurable composition may be coated onto the inorganic barrier layer by spill coating, slit coating, or the like, followed by irradiation to form an organic barrier layer thereon. The procedure of forming the inorganic and organic barrier layers may be repeated (preferably, forming a 7-layer structure of an inorganic barrier layer-organic barrier layer-inorganic barrier layer-organic barrier layer-inorganic barrier layer-organic barrier layer-inorganic barrier layer).

Although not particularly limited, the inorganic barrier layer and the organic barrier layer may be formed by deposition.

In the present invention, a method of encapsulating a member for an apparatus may include: stacking one or more members for an apparatus on a substrate; and depositing at least one barrier stack including one or more inorganic barrier layers and organic barrier layers and adjoining the member for an apparatus.

should be understood that these examples are provided for illustration only and are not to be in any way construed as limiting the present invention.

Preparative Example 1

Preparation of Silicon-Based Compound (Formula 1A)

In a temperature-controllable jacket type reactor provided with a reflux device, 100.00 g of diethylene glycol (A) ($C_4H_{10}O_3$, TCl Co., Ltd.), 35% HCl (Aldrich GmbH) in an equivalent weight of 0.05 relative to the diethylene glycol (A), and methylene chloride ($CH_2Cl_2$, TCl Co., Ltd.) in an amount corresponding to 30 wt % of solids in the total reaction solution were placed and stirred at room temperature for 30 minutes. Then, with the reactor maintained at room temperature, 2 equivalent weights of 3-(methoxy(dimethyl)silyl)propyl methacrylate ($C_{10}H_{20}O_3Si$, Gelest Inc.) relative to the diethylene glycol (A) was slowly added dropwise into the reactor. After addition of the components, the reactor temperature was set to 40° C., followed by refluxing the components for 6 hours with stirring and then cooling, thereby completing the reaction. The organic solution in the reactor was neutralized with distilled water until pH became neutral, followed by vacuum distillation and drying, thereby obtaining a final product. The final product was confirmed by NMR and GC.

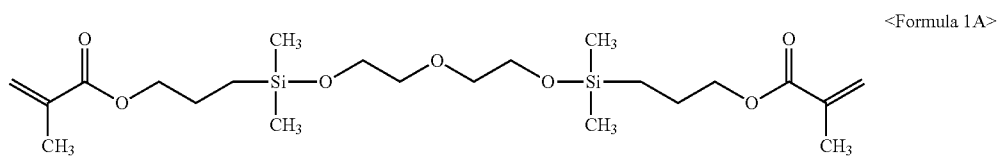 [SMILES: C=C(C)C(=O)OCCC[Si](C)(C)OCCOCCO[Si](C)(C)CCCOC(=O)C(=C)C]

<Formula 1A>

Details of the substrate, the member for an apparatus, the inorganic barrier layer, the organic barrier layer, and the barrier stack are the same as described above.

The member for an apparatus is stacked on the substrate. This may be performed using the same method as in the formation of inorganic and organic barrier layers, without being limited thereto.

The inorganic barrier layer and the organic barrier layer may be formed by a vacuum process, for example, sputtering, chemical vapor deposition, plasma chemical vapor deposition, evaporation, sublimation, electron cyclotron resonance-plasma enhanced chemical vapor deposition, and combinations thereof.

Mode for Invention

Hereinafter, the present invention will be described in more detail with reference to some examples. However, it Preparative Example 2

Preparation of Silicon-Based Compound (Formula 1B)

A silicon-based compound was prepared in the same manner as in Preparative Example 1 except that tetraethylene glycol ($C_8H_{18}O_5$, TCl Co., Ltd.) was used instead of diethylene glycol.

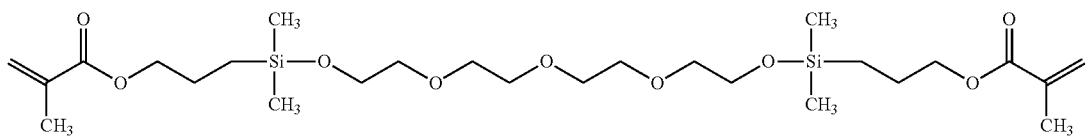

<Formula 1B>

Preparative Example 3

Preparation of Silicon-Based Compound (Formula 1C)

A silicon-based compound was prepared in the same manner as in Preparative Example 1 except that dipropylene glycol ($C_6H_{14}O_3$, TCl Co., Ltd.) was used instead of diethylene glycol.

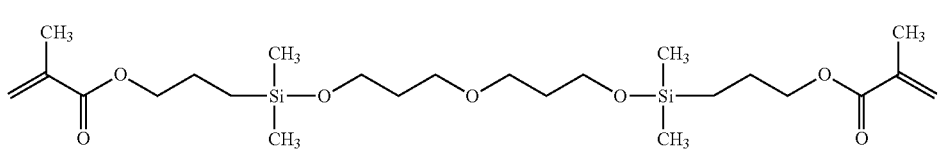
<Formula 1C>

Preparative Example 4

Preparation of Silicon-Based Compound (Formula 1D)

A silicon-based compound was prepared in the same manner as in Preparative Example 1 except that tetrapropylene glycol ($C_{12}H_{26}O_5$, TCI Co., Ltd.) was used instead of diethylene glycol.

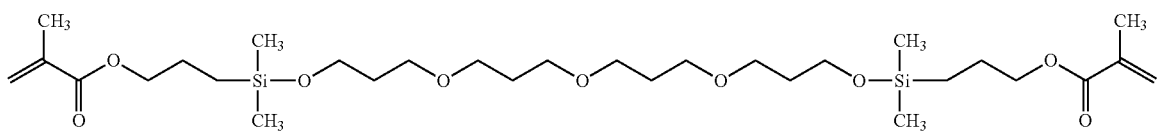
<Formula 1D>

Details of components used in Examples and Comparative Examples were as follows.

(A) Silicon-based compound including a repeating unit represented by Formula A: Compounds of Preparative Examples 1 to 4

(B) Initiator: Darocure TPO (BASF GmbH)

(C) Silicon-based compound not including a repeating unit represented by Formula A: 1,3-bis(methacryloxypropyl)tetramethyldisiloxane (D) 1,6-hexanediol diacrylate

Examples 1 to 8 and Comparative Examples 1 to 3

Photocurable compositions were prepared by mixing the components (A), (B), (C) and (D) in amounts as listed in Table 2 (unit: parts by weight, in terms of solid content), followed by stirring for 3 hours using a shaker.

The photocurable compositions prepared in Examples and Comparative Examples were evaluated as to properties. Results are shown in Table 2.

(1) Photocuring rate (%): The photocurable composition was measured as to intensity of absorption peaks in the vicinity of 1635 cm$^{-1}$ (C=C) and 1720 cm$^{-1}$ (C=O) using an FT-IR spectrometer (NICOLET 4700, Thermo Co., Ltd.). The photocurable composition was spray-coated to a thickness of 5 vim on a glass substrate, followed by UV curing through UV irradiation at 100 J/cm$^2$ for 10 seconds, thereby obtaining a specimen having a size of 20 cm×20 cm×3 μm (width×length×thickness). Then, the cured film was aliquoted, and the intensity of absorption peaks of the cured film was measured in the vicinity of 1635 cm$^{-1}$ (C=C) and 1720 cm$^{-1}$ (C=O) using an FT-IR spectrometer (NICOLET 4700, Thermo Co., Ltd.). Photocuring rate was calculated by Equation 1:

Photocuring rate (%)=|1−(A/B)|×100   <Equation 1>

(wherein Equation 1, A is a ratio of the intensity of an absorption peak in the vicinity of 1635 cm$^{-1}$ to the intensity of an absorption peak in the vicinity of 1720 cm$^{-1}$ measured for the cured film, and B is a ratio of the intensity of an absorption peak in the vicinity of 1635 cm$^{-1}$ to the intensity of an absorption peak in the vicinity of 1720 cm$^{-1}$ measured for the photocurable composition).

(2) Die share strength 1 (kgf/(mm)$^2$): Adhesive strength between glass substrates was measured in the same manner as in measurement of die shear strength. Using a Dage series 4000PXY adhesive force measurement instrument, a force of 200 kgf/(mm)$^2$ was applied at 25° C. to an upper glass substrate from a lateral side thereof to measure detachment force. A lower glass substrate had a size of 2 cm×2 cm×1 mm (width×length×thickness), the upper glass substrate had a size of 1.5 cm×1.5 cm×1 mm (width×length×thickness), and an adhesive layer had a thickness of 500 μm.

(3) Die share strength 2 (kgf/(mm)$^2$): Adhesive strength between silicon nitride layers was measured in the same manner as in measurement of die shear strength. Using a Dage series 4000PXY adhesive force measurement instrument, a force of 200 kgf/(mm)$^2$ was applied at 25° C. to an upper glass substrate from a lateral side thereof to measure detachment force. A lower glass substrate had a size of 2 cm×2 cm×1 mm (width×length×thickness), the upper substrate had a size of 1.5 cm×1.5 cm×1 mm (width×length×thickness), and an adhesive layer had a thickness of 500 μm. Both the upper and lower glass substrates were coated with silicon nitride.

(4) Reliability: A device for reliability evaluation could be fabricated by a typical method. The device was placed on a substrate, followed by deposition of an inorganic barrier layer thereon. Then, the photocurable composition was coated to a thickness of 1 μm to 5 μm onto the inorganic barrier layer by spin coating, slit coating, and the like, thereby forming an organic barrier layer. The organic barrier layers and the inorganic barrier layers were alternately formed through deposition three times. While the package was left at 85° C. and 85% RH, discoloration of the package was observed by a microscope to evaluate reliability. As shown in Table 1, a reliability score of the package was given depending on a time point at which discoloration occurred.

TABLE 1

| Time point of discoloration | Reliability score |
|---|---|
| Less than 1 week | 0 point |
| From 1 week to less than 2 weeks | 1 point |
| From 2 weeks to less than 3 weeks | 2 point |

TABLE 1-continued

| Time point of discoloration | Reliability score |
| --- | --- |
| From 3 weeks to less than 4 weeks | 3 point |
| From 4 weeks to less than 5 weeks | 4 point |
| From 5 weeks to less than 6 weeks | 5 point |
| From 6 weeks to less than 7 weeks | 6 point |
| From 7 weeks to less than 8 weeks | 7 point |
| From 8 weeks to less than 9 weeks | 8 point |
| From 9 weeks to less than 10 weeks | 9 point |
| 10 weeks or longer | 10 point |

TABLE 2

| | Example 1 | Example 2 | Example 3 | Example 4 | Example 5 | Example 6 | Example 7 | Example 8 | Comparative Example 1 | Comparative Example 2 | Comparative Example 3 |
| --- | --- | --- | --- | --- | --- | --- | --- | --- | --- | --- | --- |
| (A) Preparative Example 1 | 98 | 49 | 0 | 0 | 0 | 0 | 0 | 0 | 0 | 0 | 0 |
| Preparative Example 2 | 0 | 0 | 98 | 49 | 0 | 0 | 0 | 0 | 0 | 0 | 0 |
| Preparative Example 3 | 0 | 0 | 0 | 0 | 98 | 49 | 0 | 0 | 0 | 0 | 0 |
| Preparative Example 4 | 0 | 0 | 0 | 0 | 0 | 0 | 98 | 49 | 0 | 0 | 0 |
| (B) | 2 | 2 | 2 | 2 | 2 | 2 | 2 | 2 | 2 | 2 | 2 |
| (C) | 0 | 49 | 0 | 49 | 0 | 49 | 0 | 49 | 49 | 0 | 98 |
| (D) | 0 | 0 | 0 | 0 | 0 | 0 | 0 | 0 | 49 | 98 | 0 |
| Photocuring condition | 100 J/cm² · 10 seconds | | | | | | | | | | |
| Photocuring rate (%) | 93.9 | 94.1 | 94.0 | 94.1 | 94.0 | 93.9 | 94.1 | 94.0 | 94.0 | 93.9 | 94.0 |
| Die share strength 1 (kgf/(mm)²) | 42 | 40 | 45 | 42 | 39 | 32 | 36 | 32 | 17 | 15 | 19 |
| Die share strength 2 (kgf/(mm)²) | 43 | 41 | 44 | 39 | 37 | 30 | 34 | 28 | 15 | 12 | 18 |
| Reliability | 10 point | 10 point | 10 point | 10 point | 9 point | 8 point | 8 point | 7 point | 4 point | 3 point | 5 point |

As shown in Table 2, the photocurable composition according to the present invention exhibited high photocuring rate and high adhesion to an inorganic barrier layer formed of silicon oxide or silicon nitride after curing, while securing good reliability of the package even under severe conditions. Accordingly, the present invention provides a photocurable composition that has high photocuring rate and high adhesion to an inorganic barrier layer, and can form a barrier layer having good reliability.

On the contrary, the compositions of Comparative Examples, which were prepared using the silicon-based compound not containing the repeating unit represented by Formula A, exhibited low adhesion to an inorganic barrier layer and poor reliability.

It should be understood that the present invention is not limited to the above embodiments and the accompanying drawings and can be realized in various ways. Therefore, it should be understood that these embodiments and the accompanying drawings are given by way of illustration only and are not to be construed in any way as limiting the present invention.

The invention claimed is:

1. A photocurable composition comprising a silicon-based compound represented by Formula 1:

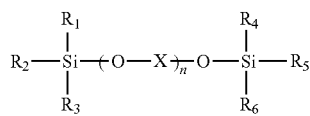

<Formula 1> wherein in Formula 1, $R_1$, $R_2$, $R_3$, $R_4$, $R_5$, and $R_6$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ silyl group, or a group represented by Formula 2,

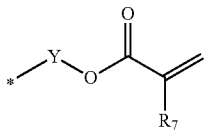

<Formula 2> wherein in Formula 2, * is a binding site to a silicon atom of Formula 1, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group;

at least one of $R_1$, $R_2$, and $R_3$ is represented by Formula 2;

at least one of $R_4$, $R_5$, and $R_6$ is represented by Formula 2;

X is a $C_1$ to $C_5$ linear or branched alkylene group; and n is an integer of 1 or more.

2. The photocurable composition according to claim 1, wherein the silicon-based compound represented by Formula 1 includes at least one of compounds represented by Formula 1-1 and Formula 1-2:

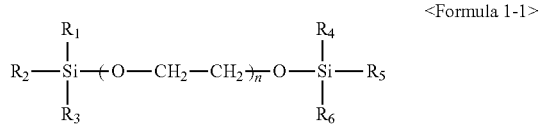
<Formula 1-1> wherein in Formula 1-1, $R_1$, $R_2$, $R_3$, $R_4$, $R_5$, and $R_6$ are the same as defined in Formula 1, and n is an integer of 1 to 10,

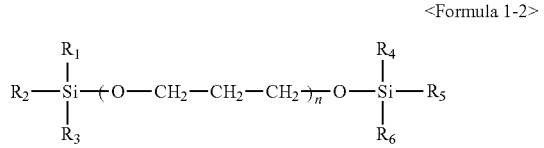
<Formula 1-2> wherein in Formula 1-2, $R_1$, $R_2$, $R_3$, $R_4$, $R_5$, and $R_6$ are the same as defined in Formula 1, and n is an integer of 1 to 10.

3. The photocurable composition according to claim 1, wherein the silicon-based compound represented by Formula 1 includes at least one of compounds represented by Formulae 1A to 1D:

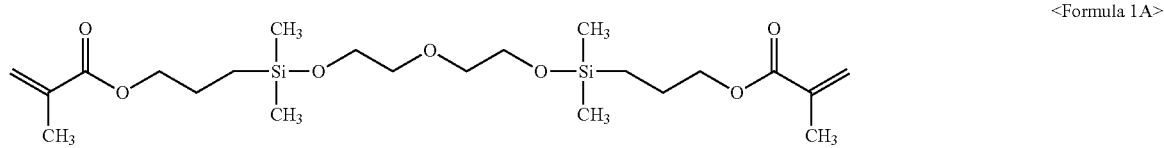
<Formula 1A>

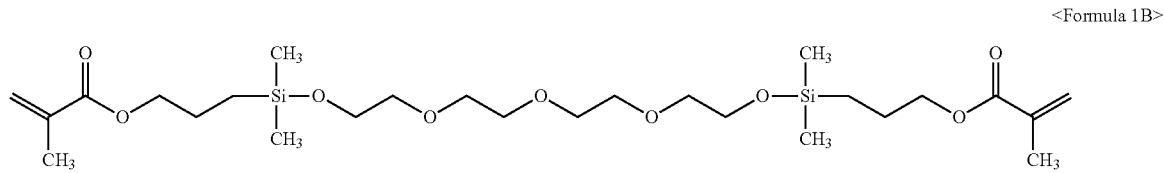
<Formula 1B>

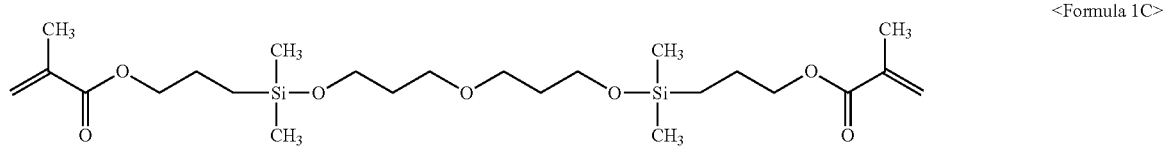
<Formula 1C>

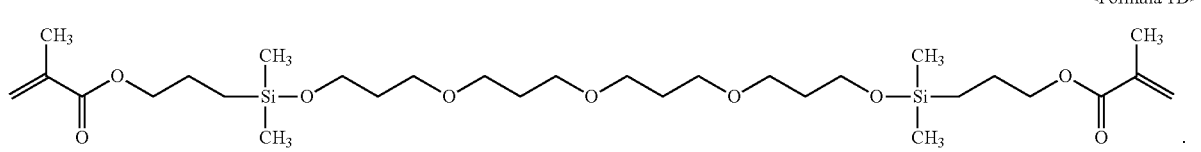
<Formula 1D>

4. The photocurable composition according to claim 1, further comprising an initiator.

5. The photocurable composition according to claim 4, wherein the initiator includes a photo initiator.

6. A photocurable composition comprising about 90 wt % to about 99 wt % of a silicon-based compound having a repeating unit represented by Formula A and a photocurable functional group:

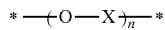
<Formula A> wherein Formula A, * is a binding site to an element; X is a $C_1$ to $C_5$ linear or branched alkylene group, and n is an integer of 1 or more, and about 1 wt % to about 10 wt % of an initiator in terms of solid content.

7. The photocurable composition according to claim 6, further including a silicon-based compound represented by Formula 3:

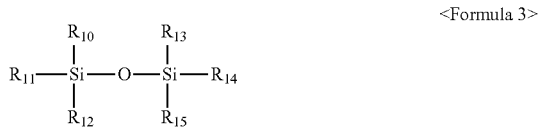
<Formula 3> wherein in Formula 3, $R_{10}$, $R_{11}$, $R_{12}$, $R_{13}$, $R_{14}$, and $R_{15}$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ alkoxy group, a substituted or unsubstituted $C_1$ to $C_{10}$ silyl group, or a group represented by Formula 2,

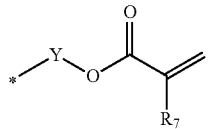
<Formula 2> wherein in Formula 2, * is a binding site to an element, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group;

at least one of $R_{10}$, $R_{11}$, and $R_{12}$ is represented by Formula 2; and at least one of $R_{13}$, $R_{14}$, and $R_{15}$ is represented by Formula 2.

8. The photocurable composition according to claim 7, wherein the silicon-based compound represented by Formula 3 includes 1,3-bis((meth)acryloxyalkyl)tetraalkyldisiloxane.

9. The photocurable composition according to claim 7, wherein the photocurable composition includes about 40 wt % to about 55 wt % of the silicon-based compound represented by Formula 1, about 1 wt % to about 5 wt % of the initiator, and about 40 wt % to about 55 wt % of the silicon-based compound represented by Formula 3.

10. An encapsulated apparatus, comprising:
a member; and
a barrier stack formed on the member, the barrier stack including an inorganic barrier layer and an organic barrier layer,
wherein the organic barrier layer includes a cured product of a photocurable composition, the photocurable composition including a silicon-based compound having a repeating unit represented by Formula A and a photocurable functional group:

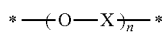
<Formula A> wherein Formula A, * is a binding site to an element; X is a $C_1$ to $C_5$ linear or branched alkylene group, and n is an integer of 1 or more.

11. The encapsulated apparatus according to claim 10, wherein the organic barrier layer and the inorganic barrier layer are alternately layered in the barrier stack.

12. The encapsulated apparatus according to claim 10, wherein the member for the apparatus includes a flexible organic light emitting device, an organic light emitting diode device, an illumination device, a metal sensor pad, a microdisc laser, an electrochromic device, a photochromic device, an microelectromechanical system, a solar cell, an integrated circuit, a charge coupled device, a light emitting polymer, or a light emitting diode.

13. The photocurable composition according to claim 6, wherein the silicon-based compound is represented by Formula 1:

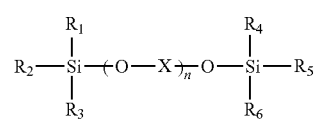
<Formula 1> wherein in Formula 1, $R_1$, $R_2$, $R_3$, $R_4$, $R_5$, and $R_6$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ alkoxy group, a substituted or unsubstituted $C_1$ to $C_{10}$ silyl group, or a group represented by Formula 2,

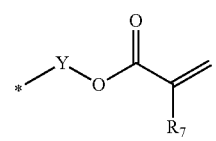
<Formula 2> wherein in Formula 2, * is a binding site to a silicon atom of Formula 1, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group;

at least one of $R_1$, $R_2$, and $R_3$ is represented by Formula 2;

at least one of $R_4$, $R_5$, and $R_6$ is represented by Formula 2;

X is a $C_1$ to $C_5$ linear or branched alkylene group; and n is an integer of 1 or more.

14. The encapsulated apparatus according to claim 6, wherein the silicon-based compound is represented by Formula 1:

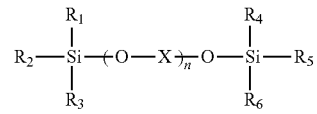
<Formula 1> wherein in Formula 1, $R_1$, $R_2$, $R_3$, $R_4$, $R_5$, and $R_6$ are each independently hydrogen, a substituted or unsubstituted $C_1$ to $C_{10}$ alkyl group, a substituted or unsubstituted $C_1$ to $C_{10}$ alkyl group having a hetero atom, a substituted or unsubstituted $C_2$ to $C_{20}$ alkenyl group, a substituted or unsubstituted $C_2$ to $C_{20}$ alkenyl group having a hetero atom, a substituted or unsubstituted $C_6$ to $C_{20}$ aryl group, a substituted or unsubstituted $C_6$ to $C_{20}$ aryl group having a hetero atom, a substituted or unsubstituted $C_1$ to $C_{10}$ alkoxy group, a substituted or unsubstituted $C_1$ to $C_{10}$ silyl group, or a group represented by Formula 2, <Formula 2>

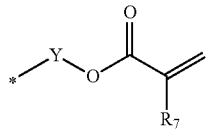

wherein in Formula 2, * is a binding site to a silicon atom of Formula 1, $R_7$ is hydrogen or a substituted or unsubstituted $C_1$ to $C_{30}$ alkyl group, and Y is a single bond, a substituted or unsubstituted $C_1$ to $C_{10}$ alkylene group, a substituted or unsubstituted $C_1$ to $C_{10}$ alkylene group having a hetero atom, a substituted or unsubstituted $C_2$ to $C_{20}$ alkenylene group, a substituted or unsubstituted $C_2$ to $C_{20}$ alkenylene group having a hetero atom, a substituted or unsubstituted $C_6$ to $C_{20}$ arylene group, a substituted or unsubstituted $C_6$ to $C_{20}$ arylene group having a hetero atom, or a substituted or unsubstituted $C_1$ to $C_{10}$ alkoxylene group;

at least one of $R_1$, $R_2$, and $R_3$ is represented by Formula 2;

at least one of $R_4$, $R_5$, and $R_6$ is represented by Formula 2;

X is a $C_1$ to $C_5$ linear or branched alkylene group; and n is an integer of 1 or more.

* * * * *